United States Patent [19]

Lecloux et al.

[11] Patent Number: 4,542,245

[45] Date of Patent: Sep. 17, 1985

[54] PROCESS FOR THE PREPARATION OF 2,2,2-TRIFLUOROETHANOL

[75] Inventors: André Lecloux, Meise; Franz Legrand, Quaregnon, both of Belgium

[73] Assignee: SOLVAY & Cie (Societe Anonyme), Brussels, Belgium

[21] Appl. No.: 575,219

[22] Filed: Jan. 30, 1984

[30] Foreign Application Priority Data

Feb. 2, 1983 [FR] France ............................... 83 01837

[51] Int. Cl.$^4$ ..................... C07C 31/38; C07C 29/48
[52] U.S. Cl. ..................................... 568/842; 502/348
[58] Field of Search ....................................... 568/842

[56] References Cited

U.S. PATENT DOCUMENTS

| | | | |
|---|---|---|---|
| 2,700,686 | 1/1955 | Dickey et al. | 568/842 |
| 3,146,274 | 8/1964 | Brill | 260/633 |
| 3,367,982 | 2/1968 | Merritt | 260/633 |

OTHER PUBLICATIONS

*Chemical Abstracts*, vol. 69, No. 5, Jul. 29th, 1968, p. 1726, Paragraph 18477v, Belen'kii et al., "Potassium Permanganate in Hypofluorination Reactions".

*Chemical Abstracts*, vol. 64, No. 9, Apr. 25th, 1966, paragraph 12534c, L. S. German et al., "Hypofluorination Reaction".

*Chemical Abstracts*, vol. 66, No. 15, Apr. 10th, 1967, p. 6093, paragraph 64988y, L. S. German et al., "Hydrogen Peroxide in the Hypofluorination Reaction".

*Primary Examiner*—J. E. Evans
*Attorney, Agent, or Firm*—Spencer & Frank

[57] ABSTRACT

2,2,2-Trifluoroethanol is obtained by catalytic oxidation of 1,1-difluoroethylene.

The 2,2,2-trifluoroethanol thus obtained is used as a solvent or as a synthesis intermediate.

13 Claims, No Drawings

PROCESS FOR THE PREPARATION OF 2,2,2-TRIFLUOROETHANOL

The present invention relates to a process for the preparation of 2,2,2-trifluoroethanol from 1,1-difluoroethylene and an oxidising agent, such as oxygen.

It is known from the Russian publications Izv. Akad. Nauk., SSSR Ser Khim. 1968 (3) pages 554–558 and Dokl. Akad. Nauk., SSSR, 1966, 166 (3) pages 602–603, reviewed respectively in Chemical Abstracts 1968, 69, No. 18477v and Chemical Abstracts 1966, 64, page 12534 (c), that 2,2,2-trihalogenoethanols corresponding to the formula $$CX_1X_2F-CH_2OH$$

in which $X_1$ and $X_2$ are identical or different and represent fluorine or chlorine, can be obtained by hypofluorination of 1,1-dihalogenoethylenes of the formula $CX_1X_2=CH_2$ in the presence of an oxidising agent. These publications disclose that, in order to obtain, in particular, 2,2,2-trifluoroethanol, 1,1-difluoroethylene is added slowly and in well-defined proportions to a mixture which contains equally well-defined proportions of anhydrous hydrofluoric acid, absolute ether and chromium trioxide ($CrO_3$) and is kept at −78° C. The use of potassium permanganate ($KMnO_4$) as the oxidising agent is also disclosed therein.

This process for the preparation of 2,2,2-trihalogenoethanols $CX_1X_2F-CH_2OH$, and in particular 2,2,2-trifluoroethanol, presents serious difficulties when its industrial utilisation is envisaged. In fact, anhydrous hydrofluoric acid is used, which means that expensive corrosion-resistant materials must be used and it is necessary to carry out the process at a very low temperature.

The present invention means that the above disadvantages can be avoided, and provides a process which can be carried out under more economical conditions and in the materials usually employed on an industrial scale. Moreover, the invention provides a process which can be carried out continuously.

To this effect, the invention relates to a process for the preparation of 2,2,2-trifluoroethanol from 1,1-difluoroethylene under the influence of, in particular, an oxidising agent, in which the 1,1-difluoroethylene is reacted with an oxidising agent in the presence of an oxidation catalyst.

Any oxidising agent can be used in the process according to the invention, but an oxidising agent chosen from the oxidising agents generally used for oxidising any hydrocarbon derivatives, and in particular for oxidising ethylenically unsaturated derivatives into corresponding alkanol derivatives is usually employed. In general, the oxidising agent is chosen from substances containing only oxygen, such as atomic oxygen, molecular oxygen and ozone, or from organic oxidising agents, such as organic peroxides and peracids, such as peracetic acid and performic acid, or from inorganic oxidising agents, such as hydrogen peroxide, metal oxides and peroxides and salts. such as metal permanganates and perchromates. Atomic oxygen, molecular oxygen or ozone is preferably used as the oxidising agent. The best results are obtained when molecular oxygen is used.

All the catalysts usually employed in catalytic oxidation reactions, and in particular oxidation catalysts chosen from metals or metal derivatives, such as oxides, halides and carboxylates, can be used in the process according to the invention. In general, the process is carried out with metals or derivatives of those metals of groups Ib, IIb, IIIb, Ivb, Vb, VIb, VIIb and VIIIb of the periodic table of the elements from the international classification of the elements (Handbook of Chemistry and Physics, 51st edition, 1970–1971). Preferably, metals from groups Ib, IIb, IIIb, Ivb and Vb or the corresponding oxides are used. The best results are obtained using silver as the oxidation catalyst.

The oxidation catalysts according to the invention can be used as such or associated with other materials which act as supports. In general, they are used in association with a support. In this case, the supports are chosen such that one or more of the characteristics of the oxidation catalysts, such as mechanical strength, particle size and distribution, pore volume, specific surface area, catalytic activity, catalytic productivity or selectivity, are improved.

To this effect, all the materials generally used as catalyst supports can be employed, that is to say, for example, metals, metal oxides, oxide derivatives of metalloids and of rare earths, diatomaceous earths, pumice, bentonites, active carbons and silica gels. Preferably, the supports are chosen from the oxides of elements of groups IIa, IIIa and Iva of the periodic table of the elements. Particularly suitable supports are aluminium oxides or aluminas. Of these, those having a specific surface area below 5 $m^2/g$, and in particular those having a specific surface area below 1 $m^2/g$, are advantageously selected. Good results have been obtained with specific surface areas of between 0.01 and 0.5 $m^2/g$. Particularly preferred supports are the aluminas of the alpha type.

Good results are obtained if the support selected is an alumina in the form of small porous or non-porous granules of average diameter between 0.005 and 5 cm. The best results have been obtained with alumina grains of average diameter between 0.01 and 0.5 cm.

The oxidation catalyst can be associated with the support in all proportions. If the process is carried out with silver supported on an alumina of the alpha type, an amount of silver of between 0.1 and 100 g per 100 g of alumina of the alpha type is in general used. An amount of between 1 and 50 g of silver per 100 g of alumina of the alpha type is preferably chosen.

In the procedure for the process according to the invention which consists of using silver supported on an alumina of the alpha type as the oxidation catalyst, it has been found that the purity of the alpha-alumina is of great significance. It is thus advantageous to choose an alumina of the alpha type which is as pure as possible. Preferably, an alumina of the alpha type containing less than 2% by weight of impurities, and in particular impurities containing metals, such as iron, is chosen. An alumina of the alpha type containing less than 0.6% by weight of iron, based on the weight of the aluminium contained in the alumina, is advantageously chosen. An alumina of the alpha type containing less than 0.2% by weight of iron, based on the content of aluminium in the alumina, is particularly advantageously chosen.

The oxidation catalyst can be incorporated in the support according to any of the known techniques, and in particular by impregnation, precipitation, coprecipitation, mechanical mixing, vapour phase or liquid phase adsorption or vaporisation. If silver and an alumina of the alpha type are used, a procedure which has given good results consists in first impregnating the alumina of the alpha type with a solution consisting of a solvent (such as water), a silver salt dissolved in this solvent, a nitrogen base (such as ammonia or amines) and an organic reducing agent (such as formaldehyde and certain organic amines), and then removing the solvent and finally subjecting the solid obtained to heat treatment. The best results have been obtained if the impregnation of the alumina of the alpha type is carried out in the presence of chemical agents, also called promoters, which enable the dispersion of the silver in the alumina of the alpha type to be improved and this dispersed state to be maintained over a period of time. Examples of such promoters are salts or basic compounds derived from alkali metals or alkaline earth metals, such as sodium hydroxide or potassium hydroxide, and the acetates of these same metals.

The process according to the invention can be carried out in the liquid phase or in the gas phase in the presence or absence of diluents. Diluents are understood as meaning compounds which are chemically inert in the reaction for the preparation of 2,2,2-trifluoroethanol of the process according to the invention. For the process carried out in the liquid phase, the diluents are inorganic or organic solvents, such as halogenated solvents, for example carbon tetrachloride. For the process carried out in the gas phase, these diluents are gases, such as nitrogen or carbon dioxide. The reaction is usually carried out in the gas phase in the presence or absence of a diluent. The oxidation catalyst can be located in a fluidised bed or in a fixed bed. Good results have been obtained carrying out the reaction in the gas phase with the oxidation catalyst arranged in a fixed bed.

In principle, the 1,1-difluoroethylene and the oxidising agent can be reacted in any proportions in the process according to the invention. However, if the reaction is carried out in the gas phase, certain mixtures of 1,1-difluoroethylene and the oxidising agent, called "reaction mixtures" below, may be explosive and it is appropriate to determine the explosibility limits for each composition of the reaction mixture in order to define the conditions for the preparation of 2,2,2-trifluoroethanol which present only little or no risk of explosion. Thus, if the reaction is carried out with a reaction mixture consisting of 1,1-difluoroethylene and undiluted molecular oxygen, it is found that explosive reaction mixtures are formed when, at the temperatures and pressures described in the examples, the reaction mixture contains more than 10% by volume of molecular oxygen. However, it is evident that the explosive compositions of the reaction mixture are a function not only of the temperature and pressure but also of the presence or absence of other compounds, such as the abovementioned diluents.

It has been found that, in the process according to the invention, the reaction temperature is a function of the nature of the oxidising agent and the oxidation catalyst used, and varies depending on whether the reaction is carried out in the liquid phase or in the gas phase. If the reaction is carried out in the gas phase with molecular oxygen and with an oxidation catalyst consisting of silver supported on an alumina of the alpha type, a temperature of between 150° and 350° C. is usually chosen. The best results have been obtained when the temperature has been chosen between 250° and 300° C.

In the process according to the invention, a pressure is applied, which varies depending on whether the reaction is carried out in the liquid phase or in the gas phase. In the gas phase, for reasons of productivity, a partial pressure of 1,1-difluoroethylene which is as high as possible is preferably applied. The pressures applied are usually between atmospheric pressure and 100 bar. In the laboratory, good results have been obtained when the pressure applied was about 10 bar.

It has been found that the oxidation catalysts according to the invention can be used over relatively long reaction times without their activity being substantially affected, and the process according to the invention can therefore be carried out continuously or discontinuously.

The apparatus for carrying out the process according to the invention does not necessitate any particular procedure or any particular material. Any apparatus in which the abovementioned temperatures and pressures can be applied and which allow removal of the excess heat may be suitable.

The 2,2,2-trifluoroethanol obtained by the process according to the invention can be used, as such or after separation from the reaction mixture and from any byproducts obtained, in all the applications known for this product, and in particular as a solvent for fluorinated polymers or as a reactant which can be oxidised with the aim of preparing the corresponding aldehyde or acid.

The invention is illustrated by the examples described below.

EXAMPLE 1

1. Preparation of the catalyst 8 g of silver acetate dissolved in 8 cm$^3$ of 13N NH$_4$OH are introduced into a 250 cm$^3$ flask. 50 mg of sodium in the form of sodium acetate, 0.5 mg of potassium in the form of potassium hydroxide and 1.2 ml of triethanolamine are added to the solution, with stirring. After homogenisation, 120 g of alumina of the alpha type containing less than 0.1% by weight of iron and having a specific surface area of 0.3 m$^2$/g and an average particle diameter of 0.25 mm are impregnated with this solution. This mixture is heated in a drying cabinet at 100° C. for 2 hours. The solid recovered is then heated at 300° C. under a stream of nitrogen for 4 hours. The catalyst obtained contains 4% by weight of finely divided silver supported on alumina of the alpha type.

2. Oxidation reaction 5 cm$^3$ of catalyst prepared as described above are arranged in a fixed bed in a tube reactor consisting of a stainless steel tube 3/8" in diameter, and are heated at 280° C. A gaseous mixture consisting of 90% by volume of 1,1-difluoroethylene and 10% by volume of molecular oxygen is passed continuously over this catalyst at a flow rate of 15 cm$^3$ N/minute under a pressure of 8 bars. As indicated above, the proportions of 1,1-difluoroethylene and oxygen in the mixture are chosen such that a non-explosive mixture is formed. The various constituents of the reaction mixture are analysed directly at the outlet of the tube by vapour phase chromatography. The constituents analysed in the course of time are shown in the table below.

TABLE

| Constituent in % by volume | Time in hours | | | | | | | |
|---|---|---|---|---|---|---|---|---|
| | 1.5 | 3 | 4.5 | 6 | 7.5 | 9 | 10.5 | 12 |
| O$_2$ | 1.5 | 1.4 | 1.2 | 1.3 | 1.3 | 1.5 | 1.7 | 2.0 |
| 1,1-difluoro- | 85.9 | 85.7 | 85.6 | 85.4 | 85.5 | 85.6 | 85.5 | 85.5 |

TABLE-continued

| Constituent in % by volume | Time in hours | | | | | | | |
|---|---|---|---|---|---|---|---|---|
| | 1.5 | 3 | 4.5 | 6 | 7.5 | 9 | 10.5 | 12 |
| ethylene | | | | | | | | |
| 2,2,2-trifluoroethanol | 5.9 | 6.0 | 6.1 | 6.1 | 6.1 | 5.9 | 5.7 | 5.4 |
| $CO_2$ | 7.0 | 6.9 | 7.0 | 6.9 | 6.8 | 6.6 | 6.5 | 6.2 |

In this example, the selectivity for trifluoroethanol, based on 1,1-difluoroethylene consumed, is constant and about 65%. $CO_2$ is the main by-product.

EXAMPLE 2

1. Preparation of the catalyst

The catalyst was prepared as described in Example 1, except that the amounts of silver salt, sodium salt and potassium salt used were doubled.

2. Oxidation reaction

The operating conditions are identical to those described in Example 1, but a gaseous mixture consisting of $(90-X)$ % by volume of 1,1-difluoroethylene, 10% by volume of oxygen and X% by volume of $CO_2$ is passed continuously over the catalyst at a flow rate of 30 cm³ N minute, under a total pressure of 8 bar.

The table below gives, for various mixtures, the respective contents of 2,2,2-trifluoroethanol after a reaction time of 3 hours (brought to the same initial partial pressure of 1,1-difluoroethylene), the contents found for the mixture containing no $CO_2$ being set equal to 1.

TABLE

| X | 2,2,2-trifluoroethanol |
|---|---|
| 0 | 1 |
| 11 | 0.98 |
| 19 | 0.95 |
| 50 | 0.95 |

In all cases, the selectivity for 2,2,2-trifluoroethanol, based on the 1,1-difluoroethylene consumed, is about 65%. $CO_2$ is the main by-product. This example shows that the presence of a diluent, such as carbon dioxide, does not affect the reaction and that the productivity is proportional to the partial pressure of 1,1-difluoroethylene.

We claim:

1. Process for the preparation of 2,2,2-trifluoroethanol from 1,1-difluoroethylene comprising, reacting 1,1-difluoroethylene with an oxidizing agent selected from the group consisting of ozone, atomic oxygen and molecular oxygen in the presence of an oxidation catalyst.

2. Process according to claim 1, wherein the oxidizing agent is molecular oxygen.

3. Process according to claim 1, wherein the oxidation catalyst is chosen from metals or derivatives thereof.

4. Process according to claim 3, wherein the oxidation catalyst is a metal or an oxide of a metal selected from groups Ib, IIb, IIIb, IVb or Vb of the periodic table of the elements.

5. Process according to claim 4, wherein the metal is silver.

6. Process according to claim 3, wherein the oxidation catalyst is associated with a support.

7. Process according to claim 6, wherein the support is an oxide of an element of groups IIa, IIIa or IVa of the periodic table of the elements.

8. Process according to claim 7, wherein the support is aluminum oxide of the alpha type.

9. Process according to claim 1, carried out in the gas phase.

10. Process according to claim 9, carried out in the presence of gaseous diluents which are chemically inert to the reactants and the catalyst under the reaction conditions.

11. Process according to claim 5, conducted in the gas phase at a reaction temperature of from 150° to 350° C.

12. Process according to claim 12, conducted at a reaction temperature of from 250° to 300° C.

13. Process according to claim 12, conducted as a continuous process by passing the reactants in a gaseous stream through a reactor containing the catalyst.

* * * * *